(12) United States Patent
Weitzman

(10) Patent No.: US 6,330,834 B1
(45) Date of Patent: Dec. 18, 2001

(54) LIQUID SAMPLING TOOL

(76) Inventor: Gregg H. Weitzman, 4434 Calle Real, Santa Barbara, CA (US) 93111

( * ) Notice: Subject to any disclaimer, the term of this patent is extended or adjusted under 35 U.S.C. 154(b) by 0 days.

(21) Appl. No.: 09/260,918

(22) Filed: Mar. 2, 1999

Related U.S. Application Data

(60) Provisional application No. 60/117,330, filed on Jan. 22, 1999.

(51) Int. Cl.$^7$ ..................................................... G01N 1/10
(52) U.S. Cl. ..................................... 73/863.71; 73/864.73
(58) Field of Search ........................... 73/863.71, 863.72, 73/863.73, 864.73; 81/124.3, 124.7; 251/148

(56) References Cited

U.S. PATENT DOCUMENTS

| | | |
|---|---|---|
| 1,270,705 | 6/1918 | Croad . |
| 3,635,262 | 1/1972 | Stebbins . |
| 3,677,513 | * 7/1972 | Truelove ............................... 251/148 |
| 3,809,359 | 5/1974 | Truelove, Sr. . |
| 3,855,882 | * 12/1974 | Wittmann ............................ 81/124.7 |
| 4,230,002 | 10/1980 | Skidmore . |
| 4,714,138 | 12/1987 | Zaccone . |
| 4,867,017 | 9/1989 | Holman . |
| 4,905,731 | 3/1990 | Tamashiro et al. . |

FOREIGN PATENT DOCUMENTS

11069 * 1/1997 (JP) .

* cited by examiner

*Primary Examiner*—Hezron Williams
*Assistant Examiner*—Nashmiya Fayyaz
(74) *Attorney, Agent, or Firm*—Leo F. Costello

(57) ABSTRACT

A tool and method for its use in taking a sample of liquid from a tank. The tool is used to open the valve of the tank and cause a sample of the liquid in the tank to flow by gravity into a container below the tank without allowing the liquid to contact the person taking the sample. The tool is especially suited for taking samples of the fuel of a helicopter or other aircraft. The tool includes a head having an axially extending wrench socket that fits over the valve and has a transverse inner base wall to limit movement of the socket over the valve. The head has a fluid passageway extending therethrough with an upper inlet communicating with the socket and a lower outlet opening through the lower end portion. When the valve is opened by the tool, the liquid flows out of the tank, through the valve and into the passageway, through which it is channeled to the container. A handle extends radially from the head and is spaced under the tank for enabling the mechanic or other person the apply torque to the valve without the person's hand rubbing against the tank.

10 Claims, 3 Drawing Sheets

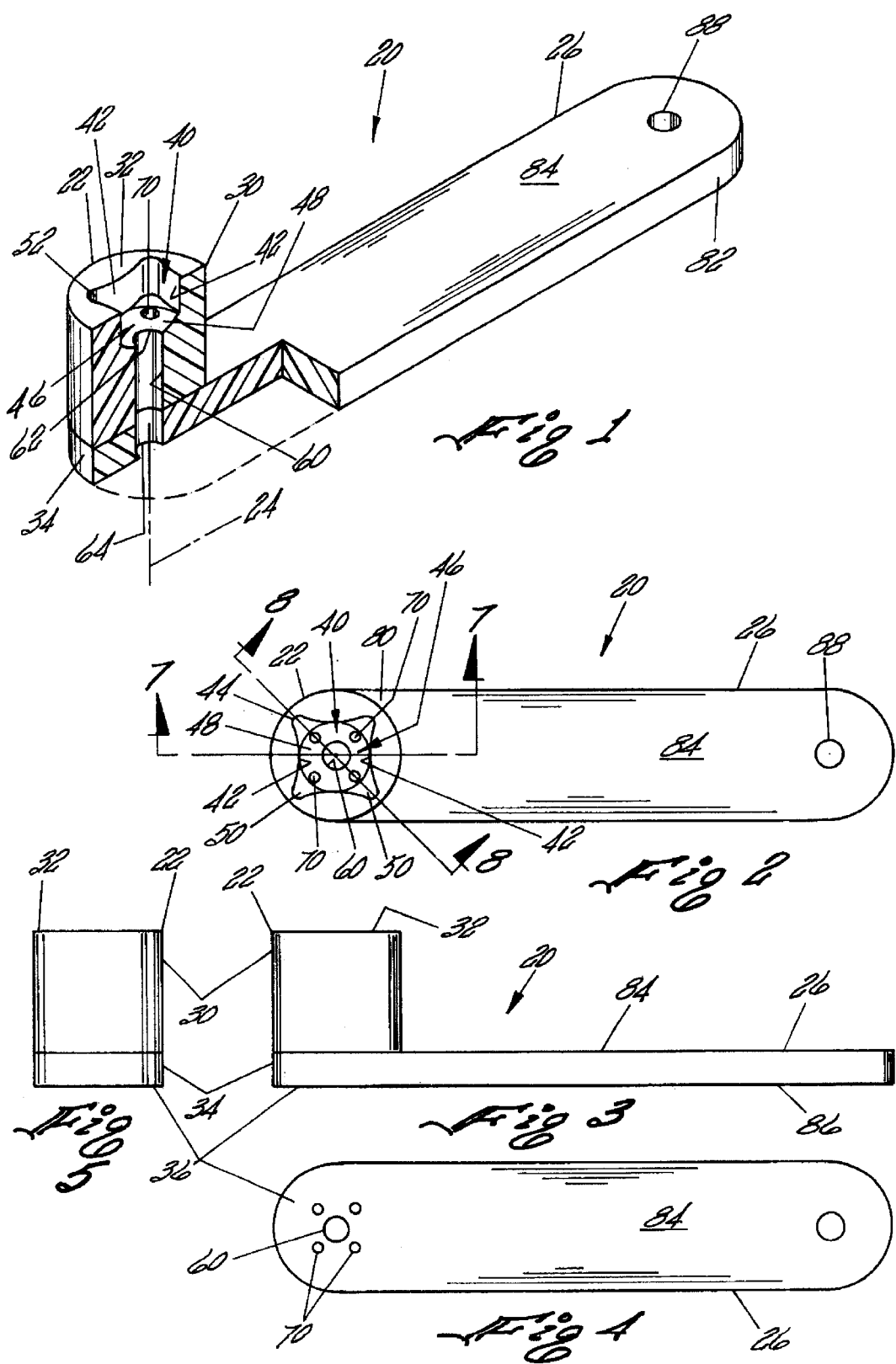

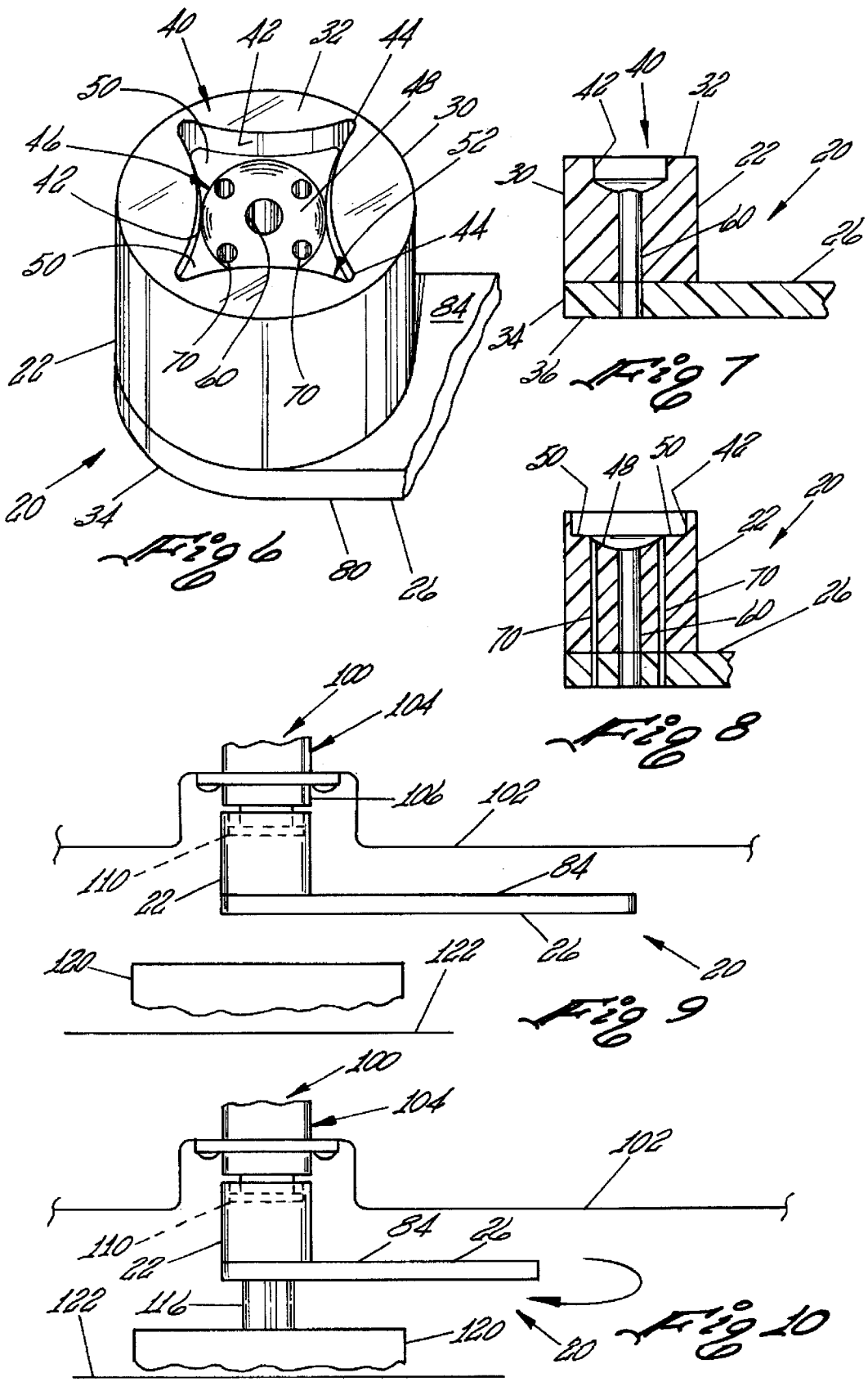

LIQUID SAMPLING TOOL

CROSS REFERENCE TO RELATED APPLICATION

This application is a regular patent application based on my prior copending provisional application No. 60/117,330, filed Jan. 22, 1999 and entitled Liquid Sampling Tool and Method of Use, which by this reference is incorporated in its entirety herein.

FIELD OF THE INVENTION

The present invention pertains to a liquid sampling tool and method of use and more particularly to tool that enables a sample of liquid to be obtained from a tank or other reservoir.

BACKGROUND

Proper maintenance of helicopters includes the task of sampling the fuel for contaminants such as water, bugs, dirt, and the like, on a regularly scheduled basis. Such sampling, for example, is performed on Bell OH-58 helicopters that are used for law enforcement purposes. The fuel tank or sump on each of these aircraft is located in the belly of the fuselage, and the drain valve through which the fuel must be drained is located under the fuselage. Periodically, a small quantity, say about one-half of a quart, is drained from the tank and analyzed. Because the belly of the aircraft where the drain valve is located is very close to the ground, the mechanic, pilot, or other person taking the sample usually lies down under the aircraft or crouches or squats down to open and close the valve in order to take the sample.

Prior to the present invention, the method followed by the person taking the sample was to place a catch basin or other receptacle on the deck under the aircraft in alignment with the drain valve, to lie or crouch down under the fuselage, and to reach up with a wrench and engage the valve handle or knob of the valve. The wrench would then be turned to open the valve and allow the small quantity of fuel to flow or drain down into the receptacle, and subsequently the valve would be closed. Unfortunately, however, this method Invariably also caused the draining fuel to run down the wrench onto the person's hand(s) and arm(s) and clothing while the wrench was being held on the valve during draining of fuel and during opening and closing of the valve. Until the subject invention, the described method, although unsatisfactory, was tolerated as the only method available to sample the fuel. Not only does this method require a special clean-up, contact of the fuel with the skin may be harmful or irritating.

Although a satisfactory tool for obtaining a sample of fuel from a helicopter fuel tank has not been previously known, tools have been available for bleeding air bubbles from hydraulic brake systems, such as used in automobiles. The U.S. Pats. Nos. 3,809,359 and 4,905,731 disclose such brake bleeder tools. These tools have general features in common with the tool of the present invention, but they are not satisfactory for taking the fuel samples as above described. In contrast, the tool of the present invention is especially suited for the task of draining aircraft fuel from helicopters, and perhaps other aircraft, or from any tank supported above the ground, floor or deck, that holds various other liquids, where the drain valve is at the bottom or sump of the tank, so that when the valve is opened, the liquid drains down out of the valve.

SUMMARY

A liquid sampling tool and method for its use in taking a sample of liquid is disclosed. The tool is used to open the drain valve of a tank and cause a sample of the liquid in the tank to flow by gravity through the tool into a container below the tank and tool without allowing the liquid to contact the person taking the sample. The tool is especially suited for taking samples of jet fuel used in a helicopter or other aircraft but is not so limited. The tool includes a head having an axially extending wrench socket that fits over the drain valve and has a transverse inner base wall to limit axial movement of the socket over the valve. The head has a fluid passageway extending therethrough with an upper inlet communicating with the socket and a lower outlet opening through the lower end portion. When the valve is opened by the tool, the liquid flows out of the tank, through the valve and into the passageway, from which it is directed into the container. A handle extends radially from the head and is spaced under the tank for enabling the mechanic or other person the apply torque to the valve without the person's hand rubbing against the tank.

An object of this invention is to facilitate the taking of samples of liquid from the sump of a tank such as is involved in sampling fuel in a helicopter.

Another object is to allow the drain valve in the sump of a tank to be opened and closed so as to drain liquid from the tank without also causing some of the liquid to flow onto the hands or arms or clothing of the person taking the sample.

An additional object is to avoid contact of liquid being drained out of a tank, especially reactive liquids such as jet fuel, with the skin of the person performing the task.

Yet another object is to allow the drain valve in the sump of a tank to be opened and closed so as to drain liquid from the tank without also causing some of the liquid to flow onto the outside of the tool being used to open and close the valve.

A further object is to provide an interfitted relationship between a drain valve on a sump of a liquid reservoir or tank and a tool for opening the valve so that the tool controls the flow of liquid draining out of the valve, causing it to pass through the tool when the valve is opened without overflow or spillage out of the tool.

Yet an additional object is to prevent chemical interaction between a tool used to open and close a valve for taking a sample of a reactive liquid, such as jet fuel, from a tank containing the liquid.

Still another object is to enable a person to use a tool to open and close a valve located under a tank without rubbing or scraping the person's hands against the undersurface of the tank.

A still further object is to facilitate the manufacture of a liquid sampling tool of the type described.

An additional object is to make a liquid sampling tool from a material that is lightweight, hard, and chemically resistant to reactive liquids.

These and other objects, features and advantages of the present invention will become apparent upon reference to the following description, accompanying drawings, and appended claims.

DESCRIPTION OF THE DRAWINGS

FIG. 1 is an isometric view of the liquid sampling tool of the present invention with the socket tilted toward the viewer, FIG. 2 is a reduced top plan view of the liquid sampling tool with the socket facing the viewer.

FIG. 3 is a side elevation of the tool shown in FIG. 2.

FIG. 4 is a bottom plan view of the liquid sampling tool of FIG. 2, showing the five drain holes of the disclosed embodiment.

FIG. 5 is an end view of the distal end of the tool shown in FIG. 2.

FIG. 6 is an enlarged isometric top view of the head of the subject tool, showing a fragment of the handle.

FIG. 7 is a fragmentary vertical cross section taken on line 7—7 in FIG. 2.

FIG. 8 is a fragmentary vertical cross section taken on line 8—8 in FIG. 2.

FIG. 9 is a side elevation of the subject tool, on a scale reduced from FIGS. 7 and 8, as the tool would be held by a mechanic to open the valve on the fuel tank of a helicopter, only a fragment of the fuselage of which is shown, in preparation for taking a sample of fuel from the tank and collecting the same in a container below the tank.

FIG. 10 is a side elevation similar to FIG. 9 but showing the tool having turned the valve one-quarter turn to open the valve and allow fuel to flow through the tool and down into the container.

DETAILED DESCRIPTION

Figure 11:
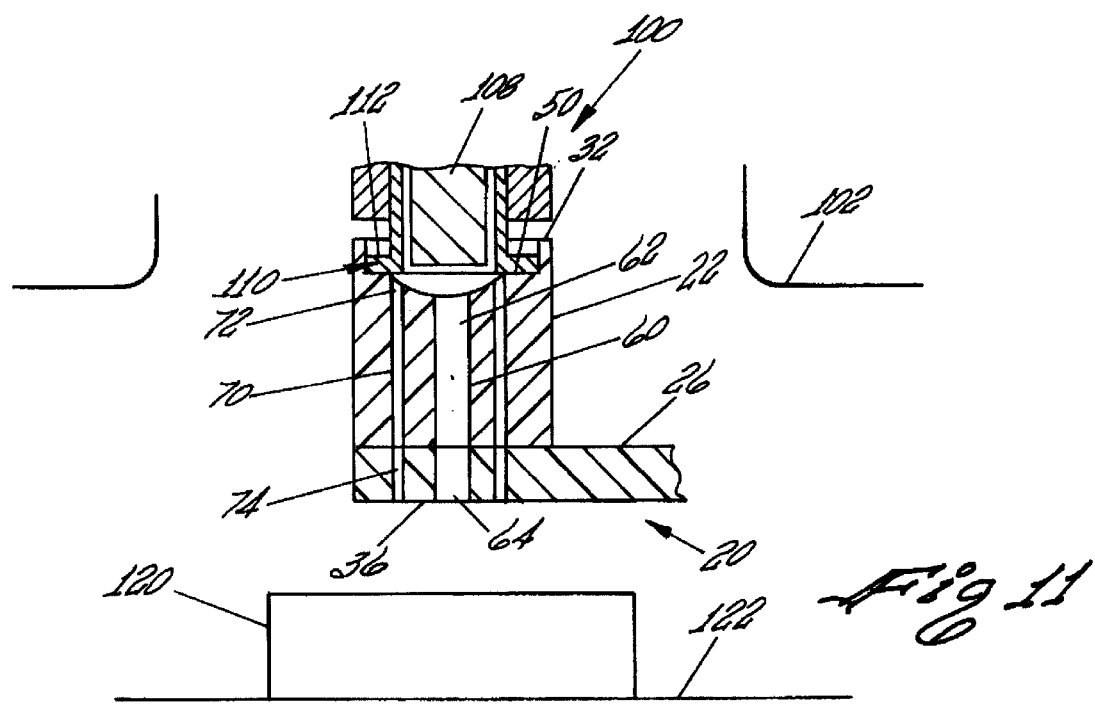
FIG. 11 is a somewhat enlarged view similar to FIG. 9 but with parts of the head of the tool and the valve in cross section.

With reference to FIGS. 1–8 in particular, the liquid sampling tool of the present invention is generally identified by the number 20. The tool has a cylindrical head, thereby providing a longitudinal axis 24, and an elongated handle 26 extending radially from the head. The tool may be made by various manufacturing processes, such as machining or molding, and may be made of various materials, such as metal or plastic, although plastic is preferred. The embodiment shown and described herein was machined from polycarbonate, which may be purchased under the trademark "LEXAN," but other plastics having the chemical resistance, hardness, and lightweight qualities herein desired may be used. Furthermore, and as stated, the tool may be molded, whereupon a plastic other than polycarbonate may be selected. Incidentally, the terms used to describe the subject tool in the following description will have reference to the typical orientation of the tool when used to open and close a drain valve as described herein.

The head 22 (FIGS. 1–8) has an upper end portion 30, terminating in a flat radial upper end surface 32, and a lower end portion 34, terminating in a flat radial lower end surface 36. The upper end portion has an axially extending, endwardly-opening wrench socket 40. This socket is defined by four axially extending, inwardly convex side walls 42 with adjacent side walls meeting in corners or junctures 44 of the socket. The side walls are disposed along arcuate surfaces that are generated by horizontal radii about centers spaced laterally outwardly of the head. The socket is further defined by an inner transverse base wall, generally indicated by the numeral 46. The base wall includes a concentric, concave depression 48, hereafter also referred to as a sump, whose periphery is tangentially related to vertical planes that are also tangential to the side walls of the socket (see esp. FIGS. 2 and 6). The base wall also has a plurality, four in the disclosed embodiment, of generally triangular or bell-shaped lateral ledges 50 that project radially outwardly from the depression 48 into the corners, that is, at the base of the corners of the socket, whereby the corners and the ledges form lateral pockets 52 of the socket.

From the foregoing description and as best shown in FIGS. 2 and 6 of the drawings, it will be understood that the socket 40 in the disclosed embodiment has the configuration of a four-pointed star and thus may be referred to as star-shaped, with the four corners 44 and ledges 50, that is the pockets 52, constituting the four points of the star. The disclosed configuration of the socket is provided so that the socket will fit a particular valve to be opened with the tool 20, in a manner to be explained. Although the particular socket configuration of the disclosed embodiment is very important in the successful functioning of the tool 20 in opening and closing the particular valve to be described, it will be understood as the description proceeds that other socket configurations to fit other valve shapes could be provided without departing from the spirit and scope of the present invention.

The head 22 (FIGS. 1–8) also provides an axially extending, concentric main bore or passageway or hole 60 having an upper end 62 communicating with the depression 48 of the socket 40 and a lower end 64 opening through the lower end surface 36 of the head. Furthermore, the head has a plurality of offset, axially extending, auxiliary bores passageways or holes 70, each of which has an upper end 72 (FIG. 11) communicating with the depression adjacent to both the periphery thereof as well as to one of the ledges 50 of the socket (FIGS. 2 and 6). Each of these auxiliary bores also has a lower end 74 opening through the lower end surface of the head. As such, the auxiliary bores are equally spaced from the main bore and are in equally spaced relation around the main bore. The main bore is of slightly larger diameter than the auxiliary bores, but each bore, main and auxiliary, is of uniform diameter throughout its respective length.

The handle 26 (FIGS. 1–8) is flat and generally rectangular and radially extends from the lower end portion 34 of the head 22. The handle thus includes a distal end 80 connected to the head, a proximate end 82, flat top and bottom surfaces 84 and 86, respectively, and a hanging hole 88 in its proximate end. The bottom surface of the handle is flush with the lower end surface 36 of the head, and the width of the handle is equal to the diameter of the head. As will be understood, the disclosed handle shape is very functional for the intended use, but it will also be understood that other shapes could be used without departing from the spirit and scope of the present invention.

Although the tool 20 is not limited to particular dimensions, there are certain dimensional relationships that are important as will be explained. To aid in describing the important dimensional relationships, the specific dimensions of the preferred embodiment are set forth at this point. The overall length of the tool from the distal end 80 to the proximate end 82 is about 9.5". The length of the head 22 from the lower end surface 36 to the upper end surface 32 is about 2.25", this dimension being referred to herein as the outside length of the head. The inside length of the head, that is the dimension from the upper end surface 32 to the top surface 84 of the handle, is about 1.75". The diameter of the head 22 as well as the width of the handle 26 is about 1.75". The depth of the socket 40 from the upper end surface 32 to the ledges 50, that is the minimum depth of the socket 40, is approximately 0.5", whereas the maximum depth of the socket from the upper end surface 32 to the nadir of the depression 48 is approximately 0.6". The maximum transverse dimension of the socket 40 from one corner 44 to the opposite corner is approximately 1.6", whereas the minimum dimension of the socket between opposing side walls 42 is approximately 1". From this, it will be understood that the diameter of the depression is about 1". Still further, the diameter of the main bore 60 is about 0.375", and the diameter of each of the auxiliary bores 70 is about 0.17".

Although dimensions have been stated in some cases to three decimal places, such specificity is not to be construed as meaning that the invention is limited to these particular dimensions, as above stated; these dimensions are merely those of the embodiment manufactured for the particular sampling task described herein. However, certain dimensional relationships are important insofar as certain features of the invention are concerned. Thus, both the inside and outside lengths of the head 22 and the dimensions of the socket, both with regard to each other and to the particular application of the tool, are important, as will be described below.

DESCRIPTION OF THE METHOD AND USE OF THE TOOL

Figure 12:
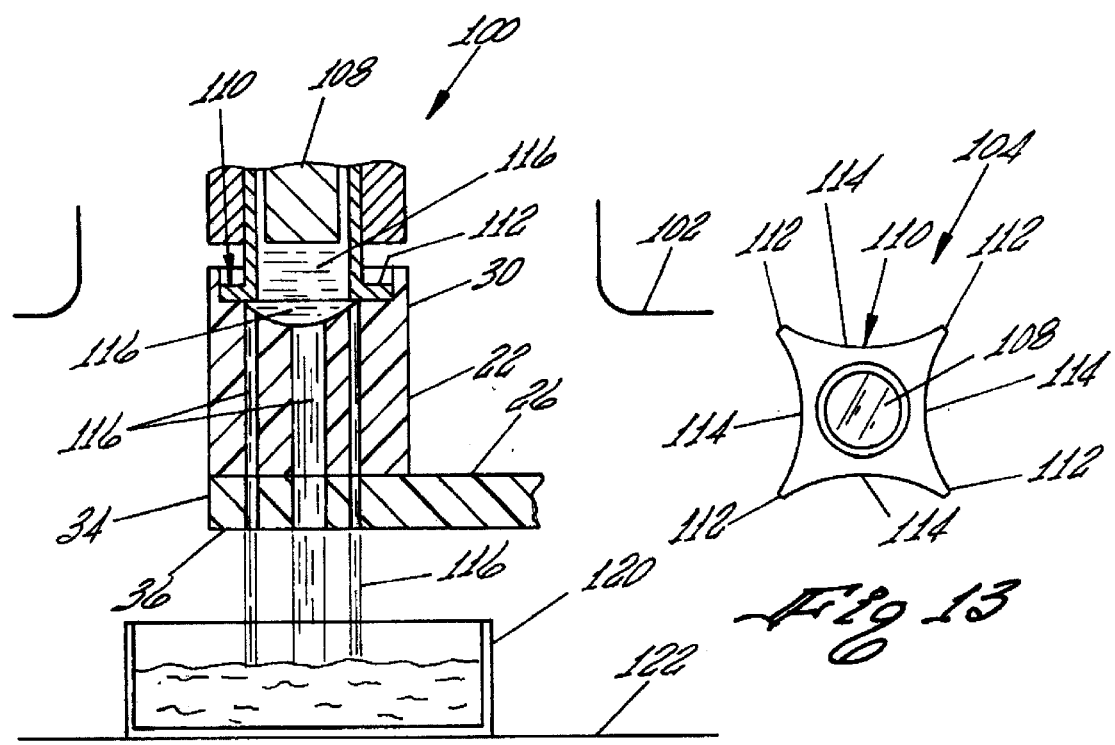
FIG. 12 is a somewhat enlarged view similar to FIG. 10 but with parts of the head of the tool and the valve in cross section and showing a sample of the liquid, that is jet fuel, flowing through the valve and into and through the tool and down into the container.
Figure 13:
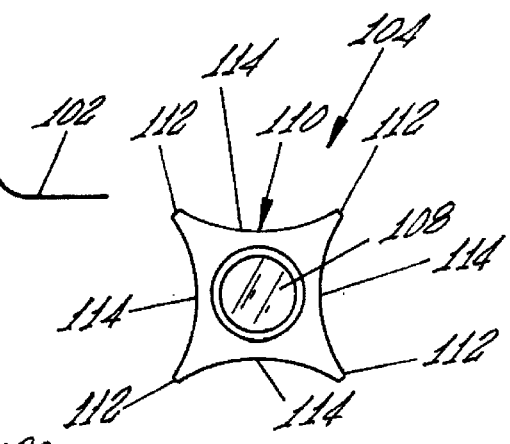
FIG. 13 is a schematic view of the face of the drain valve for which the embodiment of the tool of the present invention is especially useful.

With particular reference to FIGS. 9–13, the liquid sampling tool 20 is particularly suited for taking a sample of liquid, such as jet fuel 116, from the fuel tank, generally indicated by the numeral 100, of a helicopter, not shown, but having a fuselage generally indicated by the number 102 in the drawings. A fuel drain valve 104 is connected to the tank and projects downwardly from the fuselage in the belly of the aircraft. The valve has a valve body 106, a plunger 108, and a valve handle 110, which as shown in FIG. 13, has a star-shaped configuration similar to that of the socket 40. The valve here described and generally shown in the drawings is part No. 206-062-640-1 used on the Bell OH-58 series of helicopters. As is well known, this valve operates in generally the following manner. Assuming the valve is closed, when the valve handle is turned sufficiently in an opening direction (i.e., from the FIG. 11 position to the FIG. 12 position), the plunger is retracted, i.e., lifted, in the illustrated orientation, by a cam, not shown, that is actuated by turning the handle 110, so as to allow fuel or other liquid to pass through the valve. When the valve handle is turned in the opposite direction so as to close the valve, from the FIG. 12 position to the FIG. 11 position the plunger moves outwardly or downwardly to close the valve and preclude passage of the fuel or other liquid through the valve.

In use of the subject tool 20 (FIGS. 9–12), the mechanic or other person obtaining the fuel sample, first places a catch basin, receptacle or other container 120 on the deck 122 underneath the valve 104 on the fuel tank 100. Then, the mechanic lies or squats down on the deck under the fuselage 102 and with the tool in hand, places the socket 40 over the valve handle 110. As will be understood with particular reference to FIG. 11, movement of the socket over the valve handle causes the ledges 50 of the socket to fit up against the projections 112 of the valve handle, and the convex side walls 42 of the socket to fit in the concave sides 114 of the valve handle. The tool dimensions are determined so as to provide a close fit, so that with such a fit and with the construction of the socket, there is a space between the depression 48 and the valve handle and the upper ends 62 and 72 of the main and auxiliary bores 60 and 70 communicate with this space, as seen in FIGS. 11 and 12. It is also to be observed that because of the dimensional relationships stated above, when the tool is fully engaged with the valve as just described, the distance between the fuselage 102 and the top surface 94 of the handle 26 (FIGS. 9 and 10) is just sufficient to allow the mechanic's hand or hands to grasp the handle without contacting, scraping or rubbing against the fuselage.

With the tool 20 thusly fitted on the valve handle 110, and assuming that the valve 104 is closed, the operator then turns the tool, and thus the valve handle, approximately one quarter of a turn, in the opening direction. This action moves the tool and the valve from the closed position shown in FIG. 11 to the open position shown in FIG. 12. The plunger 108 is thereby moved from the closed position of FIG. 11 to the raised, open position of FIG. 12. Accordingly, fuel 116 is allowed to gravitate through the valve and into the depression or sump 48 of the tool from where it enters the main and auxiliary bores 60 and 70. The fuel then exits from the lower ends 64 and 74 of the bores and drains down into the catch basin 120, as illustrated in FIG. 12. After about a one-half of a quart of fuel has been collected in the basin, the mechanic turns the handle 26 in the opposite direction in order to allow the plunger 108 to return to its lower position thereby closing the valve, as shown in FIG. 11, and shutting off the flow of fuel from the valve into the tool and the catch basin. The tool is then separated from the valve, and the sample of the fuel collected in the basin taken away for analysis.

It will thus be understood that this entire process of taking a sample of fuel 116 is carried out without the fuel ever coming into contact with the mechanic who is performing the task. In other words, because the fuel is constrained or controlled to flow by gravity directly from the valve 104 into the head 22 and thence into the container 120, none of the fuel flows along the outside of the tool, or otherwise spills, onto the mechanic's hands or arms or clothing. In this regard, engagement of the ledges 50 and side walls 42 of the tool with the projections 112 of the valve 104 forms a seal precluding exit of fuel under the conditions described. Not only is the mechanic and his or her clothing protected from contact with the fuel, the tool itself is not covered with fuel except for the internal surfaces of the socket 40 and bores 60, 70. Excess fuel can easily be shaken from the head and then the socket and internal surfaces wiped out with a dry cloth. Moreover, during the sample taking, the operator does not scrape or rub his hand or hands against the fuselage 102, thereby avoiding abrasion of the skin. Still further, because the tool is made of a plastic, such as polycarbonate, that does not react with the fuel, the tool is not chemically damaged by the fuel. The material from which the tool is made causes the tool to have a high hardness number, such as may be achieved with polycarbonate. Another advantage of choosing a plastic such as polycarbonate is its lightweight thereby making the tool lightweight for stowing on the helicopter when not in use. The hanging hole 88 is conveniently provided for hanging the tool on board the helicopter.

Although a preferred embodiment of the present invention has been shown and described, various modifications, substitutions and equivalents may be used therein without departing from the spirit and scope of the invention. Accordingly, it is to be understood that the present invention has been described by way of illustration and not limitation.

What is claimed is:
1. A liquid sampling tool for opening a valve of a tank containing a liquid and allowing a sample of the liquid to flow by gravity through the valve into a container below the tank, comprising:
 a cylindrical head having a longitudinal axis and upper and lower end portions respectively terminating in radial upper and lower end surfaces,
 the upper end portion providing an axially extending wrench socket that opens endwardly of the upper end portion at the upper end surface and is circumscribed by axially extending side walls defining a plurality of junctures where adjacent side walls meet, the socket being further defined by an inner base wall spaced axially downwardly from the end surface and extending transversely of the head, the base wall including a concentric concave central depression forming a sump and a plurality of lateral ledges individually extending from the depression to said junctures, the head having a concentric main bore extending axially of the head from the depression to the lower end surface, and the head also having a plurality of auxiliary bores extending axially of the head from the depression and individually adjacent to the ledges to the lower end surface; and a handle extending radially from the lower end portion of the head.

2. The tool of claim 1, wherein the depth of the socket from the upper end surface to the base wall is less than the length of the head between the end surfaces.

3. The tool of claim 1, wherein the depth of the socket from the upper end surface to the base wall is approximately twenty percent of the length of the head between the end surfaces.

4. The tool of claim 1, wherein the length of the head between the end surfaces is approximately two and one-quarter inches.

5. The tool of claim 1, wherein the depth of the socket from the upper end surface to the base wall is approximately seven-sixteenths of an inch.

6. The tool of claim 1, wherein the length of the head between the end surfaces is approximately two and one-quarter inches; and wherein the depth of the socket from the upper end surface to the base wall is approximately seven-sixteenths of an inch.

7. The tool of claim 1, wherein the handle is elongated, flat, and generally rectangular.

8. A liquid sampling tool for opening a valve of a tank containing a liquid and allowing a sample of the liquid to flow by gravity through the valve into a container below the tank, comprising:

a head having a longitudinal axis and upper and lower end portions, the upper end portion providing an axially extending wrench socket that opens endwardly of the upper end portion and is defined by axially extending side walls, the socket being further defined by a transverse inner base wall intermediate the upper and lower end portions but located closer to the upper end portion, the head having a bore extending axially therethrough and having an upper inlet communicating with the socket and a lower outlet opening through the lower end portion, the bore having a length and opposite ends and being of substantially uniform diameter throughout the length of the bore or at least without appreciable restriction between the ends of the bore; and a handle extending radially from the head, wherein there is a depression in the base wall forming a sump, the sump having a periphery;

wherein the bore is a main bore and is concentric with the sump; and wherein there are auxiliary bores extending through the head around the main bore, each auxiliary bore having an upper inlet communicating with the sump adjacent to the periphery of the sump and a lower outlet opening through the lower end portion.

9. A liquid sampling tool for opening a valve of a tank containing a liquid and allowing a sample of the liquid to flow by gravity through the valve into a container below the tank, wherein the valve has a valve opening, comprising:

a head having a longitudinal axis and upper and lower end portions, the upper end portion providing an axially extending wrench socket that opens endwardly of the upper end portion and is defined by axially extending side walls, the socket being further defined by a transverse inner base wall intermediate the upper and lower end portions but located closer to the upper end portion, the base wall including a central depression defining a sump having a diameter approximately equal to the diameter of the valve opening, the sump having a periphery , the base wall further including ledges peripherally of the sump in substantially perpendicular relation to said axis and defining a valve seat peripherally of the sump, the head having a bore extending axially therethrough and having an upper inlet opening through the base wall into the sump and a lower outlet opening through the lower end portion; and a handle extending radially from the head, wherein the side walls of the socket are convex;

wherein adjacent side walls converge and define corners of the socket; and wherein the ledges are in the corners.

10. The tool of claim 8, walls of the socket are convex;

wherein adjacent side walls converge in corners of the socket;

wherein the base wall also includes ledges that extend from the sump into the corners; and wherein the auxiliary bores open into the sump individually adjacent the corners of the socket.

* * * * *